(12) United States Patent
Fuhrman et al.

(10) Patent No.: US 12,582,345 B2
(45) Date of Patent: Mar. 24, 2026

(54) SYSTEMS AND METHODS FOR IDENTIFYING PROGRESSION OF HYPOXIC-ISCHEMIC BRAIN INJURY

(71) Applicant: The University of Chicago, Chicago, IL (US)

(72) Inventors: Jordan D. Fuhrman, Chicago, IL (US); Ali Mansour, Chicago, IL (US); Maryellen L. Giger, Elmhurst, IL (US); Fernando D. Goldenberg, Chicago, IL (US)

(73) Assignee: The University of Chicago, Chicago, IL (US)

( * ) Notice: Subject to any disclaimer, the term of this patent is extended or adjusted under 35 U.S.C. 154(b) by 297 days.

(21) Appl. No.: 18/274,819

(22) PCT Filed: Feb. 1, 2022

(86) PCT No.: PCT/US2022/014765
§ 371 (c)(1),
(2) Date: Jul. 28, 2023

(87) PCT Pub. No.: WO2022/165431
PCT Pub. Date: Aug. 4, 2022

(65) Prior Publication Data
US 2024/0108276 A1 Apr. 4, 2024

Related U.S. Application Data

(60) Provisional application No. 63/144,234, filed on Feb. 1, 2021.

(51) Int. Cl.
*G06T 7/00* (2017.01)
*A61B 5/00* (2006.01)

(52) U.S. Cl.
CPC .......... *A61B 5/4064* (2013.01); *A61B 5/0042* (2013.01); *G06T 7/0012* (2013.01);
(Continued)

(58) Field of Classification Search
CPC ... A61B 5/4064; A61B 5/0042; G06T 7/0012; G06T 2207/10081; G06T 2207/20081;
(Continued)

(56) References Cited

U.S. PATENT DOCUMENTS

| | | | | |
|---|---|---|---|---|
| 2010/0251394 A1* | 9/2010 | Dore | ........................ | C12Q 1/25 800/9 |
| 2014/0045713 A1* | 2/2014 | Everett | .............. | G01N 33/6896 506/18 |

(Continued)

OTHER PUBLICATIONS

Antropova, N. et al., "A deep feature fusion methodology for breast cancer diagnosis demonstrated on three imaging modality datasets", American Association of Physicists in Medicine, 44(10): 5162-5171 (Oct. 2017).

(Continued)

*Primary Examiner* — Van D Huynh
(74) *Attorney, Agent, or Firm* — Cozen O'Connor

(57) ABSTRACT

A method for identifying the presence or progression of hypoxic ischemic brain injury includes, for each subset of one or more subsets of a three-dimensional medical image of a head of a patient: (i) inputting said each subset into a machine-learning model, (ii) extracting one or more features or feature maps from the machine-learning model, and (iii) constructing, based on the one or more features or feature maps, one of a sequence of vectors. The sequence of vectors is then pooled to obtain a scan-level vector that is used to obtain a score indicating HIBI presence or progression in the patient. For example, the scan-level vector can be inputted into a pre-trained classifier that generates the score based on (Continued)

the scan-level vector. The machine-learning model may be a pre-trained conventional neural network or support vector machine.

20 Claims, 7 Drawing Sheets

(52) U.S. Cl.
CPC ............... *G06T 2207/10081* (2013.01); *G06T 2207/20081* (2013.01); *G06T 2207/20084* (2013.01); *G06T 2207/30016* (2013.01)

(58) Field of Classification Search
CPC ........... G06T 2207/20084; G06T 2207/30016; A61K 9/0097
See application file for complete search history.

(56) References Cited

U.S. PATENT DOCUMENTS

| | | | | |
|---|---|---|---|---|
| 2015/0247854 A1* | 9/2015 | Burd | .................... | G01N 33/573 |
| | | | | 435/7.4 |
| 2018/0204327 A1* | 7/2018 | Matthews | ............ | A61B 5/7275 |
| 2019/0246927 A1* | 8/2019 | Väyrynen | ............. | A61B 5/7264 |
| 2020/0090028 A1* | 3/2020 | Huang | ..................... | G06N 3/08 |
| 2022/0399117 A1* | 12/2022 | Leuthardt | .............. | G16H 30/40 |
| 2023/0109043 A1* | 4/2023 | Rao | ........................... | G06N 3/08 |
| | | | | 600/408 |
| 2023/0277151 A1* | 9/2023 | Menon | ................. | A61B 6/5247 |
| | | | | 382/131 |

OTHER PUBLICATIONS

Giger, M., "Machine Learning in Medical Imaging", J Am Coll Radiol, 15: 512-20 (Mar. 2018).

Keijzer, H.M. et al., "Brain imaging in comatose survivors of cardiac arrest: Pathophysiological correlates and prognostic properties", Resuscitation, 133: 124-136 (2018).

Shin, H. et al., "Deep Convolutional Neural Networks for Computer-Aided Detection: CNN Architectures, Dataset Characteristics and Transfer Learning", IEEE Transactions on Medical Imaging, 35(5): 1285-1298 (May 2016).

Simonyan, K. et al., "Very Deep Convolutional Networks for Large-Scale Image Recognition", arXiv:1409.1556v6 [cs.CV], 1-14 (Apr. 10, 2015).

International Search Report and Written Opinion of the International Searching Authority for International Patent Application No. PCT/US2022/014765 mailed May 12, 2022, 8 pages.

* cited by examiner

| | Total (N=54) | Progression (n=29) | Nonprogression (n=25) | p value |
|---|---|---|---|---|
| Median age (IQR), yrs | 61 (16) | 59 (27) | 62 (13) | 0.77 |
| Female sex (%) | 25 (46) | 15 (52) | 10 (40) | 0.389 |
| Race (%) | | | | |
| African American | 44 (81) | 24 (83) | 20 (80) | 0.795 |
| White | 4 (7) | 2 (7) | 2 (8) | 0.877 |
| Asian | 1 (2) | 0 (0) | 1 (4) | 0.277 |
| Unknown | 5 (10) | 3 (10) | 2 (8) | 0.767 |
| Median GCS score (IQR) | 3 (3) | 3 (2) | 6 (4) | 0.011* |
| Median GCS-M (IQR) | 1 (3) | 1 (0) | 3 (3) | 0.034* |
| Pupillary reactivity (%) | 43 (80) | 20 (69) | 23 (92) | 0.036* |
| Presence of corneal reflex (%) | 29 (56) | 11 (41) | 18 (72) | 0.023* |
| Presence of VOR (%) | 26 (52) | 9 (35) | 17 (71) | 0.010* |
| Presence of gag/cough reflex (%) | 34 (64) | 15 (52) | 19 (79) | 0.038* |
| Spontaneous respiratory drive (%) | 37 (68) | 19 (65) | 18 (72) | 0.609 |
| Myoclonus (%) | 30 (56) | 18 (62) | 12 (48) | 0.3 |
| TTM (%) | 44 (81) | 27 (93) | 17 (68) | 0.018* |
| Median time to ROSC (min) | 22 (23) | 22 (20) | 17 (15) | 0.482 |
| Median time to first CT (min) | 163 (551) | 138 (182) | 220 (382) | 0.408 |
| Median time to second CT scan (min) | 3,102 (3,011) | 3,308 (2,863) | 2,938 (3,825) | 0.438 |
| Median time between CT scans (min) | 2,872 (2,991) | 2,990 (2,303) | 2,832 (2,787) | 0.398 |
| Mortality (%) | 34 (63) | 22 (76) | 12 (48) | 0.035* |
| Cause of death | | | | |
| Cardiac death | 2 (6) | 2 (9) | 0 (0) | 0.27 |
| Brain death | 2 (6) | 2 (9) | 0 (0) | 0.27 |
| WLST | 30 (88) | 18 (82) | 12 (100) | 0.107 |
| DLS | — | 0.45 (0.02) | 0.48 (0.01) | <0.001* |

FIG. 7

SYSTEMS AND METHODS FOR IDENTIFYING PROGRESSION OF HYPOXIC-ISCHEMIC BRAIN INJURY

RELATED APPLICATIONS

This application is a 35 U.S.C. § 371 filing of International Application No. PCT/US2022/014765, filed on Feb. 1, 2022, which claims priority to U.S. Provisional Patent Application No. 63/144,234, filed on Feb. 1, 2021. Each of these applications is incorporated herein by reference in its entirety.

STATEMENT REGARDING FEDERALLY SPONSORED RESEARCH OR DEVELOPMENT

This invention was made with government support under grant numbers OD025081 and RR021039 awarded by the National Institutes of Health. The government has certain rights in the invention.

BACKGROUND

Hypoxic ischemic brain injury (HIBI) is a type of brain damage frequently caused by oxygen deprivation to the brain during cardiac arrest. HIBI after cardiac arrest is a leading cause of mortality and long-term neurological disability in cardiac-arrest survivors. Despite the many advances in the field of resuscitation post cardiac arrest, HIBI leaves many survivors with severe neurological disabilities.

SUMMARY

Survivors of cardiac arrest who remain comatose at 24-72 hours, or more, after resuscitation typically undergo neuroprognostication aimed to detect signs of HIBI and predict long-term neurological function. Four main categories of tests are used: clinical examination, electrophysiology, biomarkers, and neuroimaging. The time at which these tests are performed and their association with outcome also vary. Although clinical findings, such as pupillary reflexes and somatosensory evoked potentials, remain the most robust tests associated with outcome, biomarkers, electroencephalography, and imaging have inconsistencies that make interpreting them more dubious and subject to caution. Therefore, a multimodal approach to prognostication that factors in multiple tests is often recommended.

The radiographic hallmark of HIBI is cerebral edema, commonly evaluated on HCT as effacement of sulci and diminished gray-white matter differentiation in cortical and deep brain structures. Although magnetic resonance imaging (MRI) is arguably a more accurate modality with higher resolution and capacity at identifying HIBI, it is not always feasible, and head computed tomography (HCT) remains the more prevalent and accessible neuroimaging modality for this patient population. Cerebral edema is often a progressive phenomenon that may or may not be appreciated by expert radiologists on initial HCT. Although there is presently no consensus on the optimal timing for performing brain computed tomography (CT) for neuroprognostication, most prior-art studies evaluate imaging done within the first 24 hours, in which sensitivity of detecting cerebral edema is as low as 14% and increases to approximately 60% between 24 hours and 7 days. Absolute decrease in, difference between, and ratio between gray and white matter density (GWM ratio) have been investigated in relation to neurological outcome. Although an absolute decrease in gray matter density alone is an unreliable predictor of neurological outcome, the predictive value increases when the GWM ratio is considered. The main limitations of these prior-art studies include the time at which the analyzed HCT scan was performed (time from return of spontaneous circulation (ROSC) to HCT ranges anywhere from 4 to 72 hours) and the choice of specific regions of interest within the brain to compare gray and white matter.

Developments in machine learning have considerably improved automatic execution of computer vision tasks in medical imaging, including disease detection, diagnosis, and segmentation. Notably, convolutional neural networks—a family of deep learning architectures that identify desirable image features through optimized convolutional filters—perform comparably to experienced radiologists, with the added benefits of higher reading speeds and consistency. However, these models generally require a large amount of training data, often unavailable in medical imaging. Therefore, many deep learning schemes have been developed to circumvent this obstacle. One such technique is transfer learning, or the use of a model pretrained to perform a task in one domain that is then applied to a new domain. This approach preserves features that are useful for classification of the original image domain to classify images in the transferred domain while minimizing the need for new training data.

One aspect of the present embodiments is the realization that progression of HIBI is in fact readily identifiable on an early initial HCT scan and that the lower sensitivity observed within the first 24 hours is more likely attributable to subtle changes that evade the detection threshold of the human eye. As such, in a cohort of comatose survivors of cardiac arrest with reportedly normal HCT findings on presentation, we demonstrate that machine learning can be used to successfully predict progression, or not, of HIBI based only on the initial HCT scan.

The present embodiments use deep-transfer learning to predict, based only on the initial HCT scan, whether or not HIBI will progress. Advantageously, this early prediction of HIBI progression allows the identification of two unique endotypes of cardiac arrest survivor. Early stratification of survivors of cardiac arrest into these two distinct endotypes may help select patients that do not exhibit early radiographic HIBI since these patients are more likely to benefit from early interventions aiming at preventing further HIBI-induced brain damage.

Medical providers may advantageously use the present embodiments to identify the present or absence of HIBI sooner and more accurately than prior-art HIBI diagnostic techniques. For example, when the present embodiments indicate the presence of HIBI in a patient, a medical provider may decide to initiate conversations regarding patient care with the patient's family, thereby decreasing the patient's length of stay and alleviating undue protracted anxiety that the patient's family may be subject to. When the present embodiments indicate no evidence of HIBI, the medical provider can optimize treatments including, but not limited to: (i) targeted temperature management (hypothermia) at different doses and for different durations, (ii) hemodynamic optimization by utilizing vasoactive drugs like norepinephrine, epinephrine, vasopressin, dobutamine, angiotensin II, phenylephrine, dopamine, or a combination thereof, and (iii) multimodality brain monitoring of intracranial pressure, partial brain tissue oxygenation, near-infrared spectroscopy, and microdialysis with the purpose of establishing the optimal cerebral perfusion pressure for the patient. Furthermore, since patients displaying an absence of HIBI are more likely to recover neurologically, they are more amenable to early interventions with neuroprotective drugs.

BRIEF DESCRIPTION OF THE FIGURES

FIG. 7 is a table summarizing results of a study.

DETAILED DESCRIPTION

Figure 1:
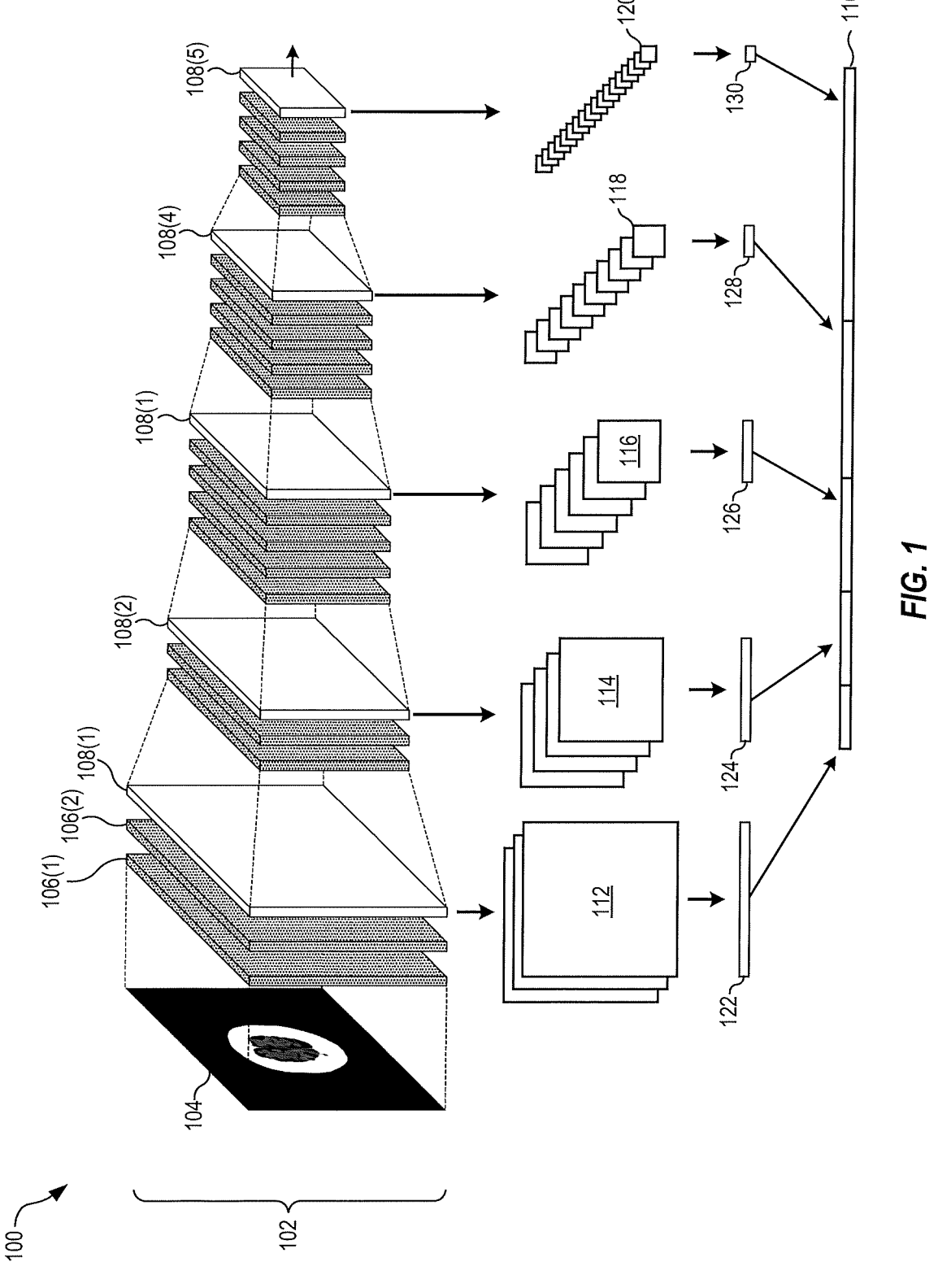
FIG. 1 illustrates a method for using a convolutional neural network (CNN) to generate a slice-level feature vector from one slice of a scan, in embodiments.
Figure 2:
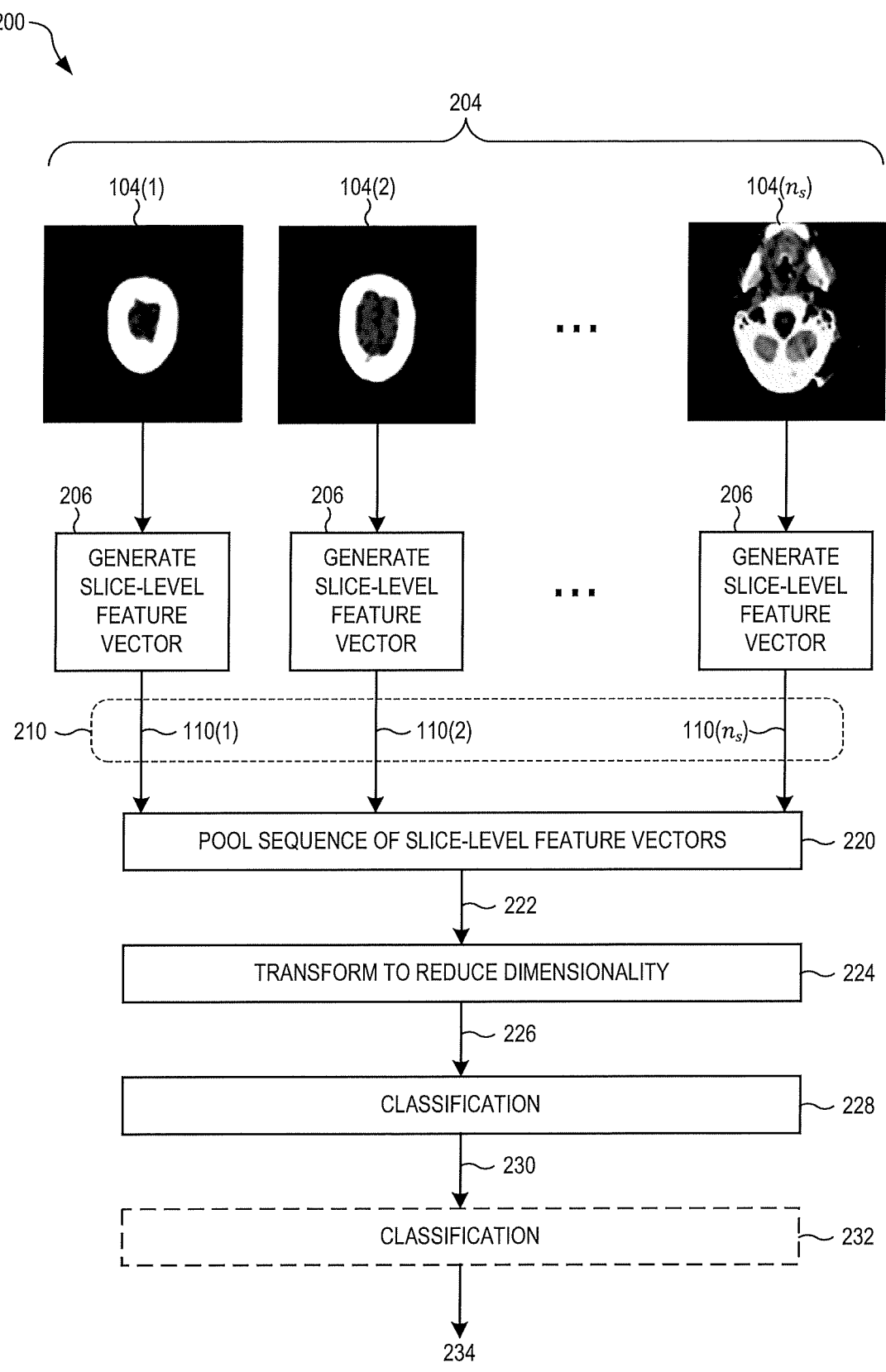
FIG. 2 illustrates a method for identifying progression of hypoxic-ischemic brain injury (HIBI), in embodiments.

FIG. 1 illustrates a method 100 for using a convolutional neural network (CNN) 102 to generate a slice-level feature vector 110 from one slice 104 of a scan (see scan 204 in FIG. 2). The scan may be, for example, a computerized tomography (CT) scan of a brain of a patient. The slice-level feature vector 110 mathematically represents the slice 104 as a point in a high-dimensional feature space. The slice 104 is a two-dimensional grayscale image that is preprocessed to match the input size of the CNN 102 (e.g., 224×224 pixels). The CNN 102 is shown in FIG. 1 as a VGG19 neural network having several convolutional layers 106, of which only the first two are labeled. The CNN 102 also has intervening pooling layers 108 used for downsampling. The CNN 102 may also have fully-connected layers and a soft-max layer, which are not shown in FIG. 1 for clarity.

Each pooling layer 108 has n channels and outputs a plurality of n two-dimensional feature maps. For VGG19, where each pooling layer 108 is a max-pool layer with a 2×2 pixel window, a first pooling layer 108(1) outputs $n_1=64$ feature maps 112, each having 112×112 pixels. For clarity, only a few of the features maps 112 are shown in FIG. 1. A second pooling layer 108(2) outputs $n_2=128$ feature maps 114, each having 56×56 pixels. A third pooling layer 108(3) outputs $n_3=128$ feature maps 116, each having 28×28 pixels. A fourth pooling layer 108(4) outputs $n_4=256$ feature maps 118, each having 14×14 pixels. Finally, a fifth pooling layer 108(5) outputs $n_5=512$ feature maps 120, each having 7×7 pixels.

The plurality of feature maps 112 are pooled and flattened into a one-dimensional array 122. For example, the feature maps 112 may be average pooled into an average feature map in which each pixel is the average of the corresponding pixels of the features maps 112. This average feature map may then be flattened to obtain the array 122. Alternatively, the feature maps 112 may be max-pooled or min-pooled. The length of the array 122 equals the number of pixels in each of the feature maps 112, or 112×112=12,544. Similarly, the feature maps 114 may be pooled and flattened into a one-dimensional array 124 of length 56×56=3,136, the feature maps 116 may be pooled and flattened into a one-dimensional array 126 of length 28×28=784, the feature maps 118 may be pooled and flattened into a one-dimensional array 128 of length 14×14=196, and the feature maps 120 may be pooled and flattened into a one-dimensional array 130 of length 7×7=49. The arrays 122, 124, 126, 128, and 130 may then be concatenated together to form the slice-level feature vector 110, which may then be normalized. The length of the slice-level feature vector 110 therefore equals the sum of the lengths of the one-dimensional arrays 122, 124, 126, 128, and 130 (i.e., 16,709 for the example of VGG19).

While FIG. 1 shows the CNN 102 as a VGG19 neural network, the CNN 102 may be another type of convolutional neural network without departing from the scope hereof. For example, the CNN 102 may be an implementation of AlexNet, ResNet (e.g., ResNet 50 or ResNet152V2), GoogLeNet/InceptionNet (e.g., InceptionV3), EfficientNet, MobileNet, DenseNet, NASNet, SENet, or another type of VGG network (e.g., VGG11, VGG16, etc.). Accordingly, the method 100 may be modified to work with any number of convolutional layers 106, any number of pooling layers 108, any image size, and any number of channels. Furthermore, where the CNN 102 is configured with multiple input channels (e.g., red, green, and blue channels for color images), the CNN 102 may be used with a grayscale image by inputting the grayscale image to all of the input channels.

The CNN 102 may already be pre-trained for image recognition, which can advantageously speed up implementation of the present embodiments given that neural-network training is typically a time- and memory-intensive process. For example, the CNN 102 may have already been pre-trained using the ImageNet dataset (e.g., by a third party such as Keras Applications). In this case, the use of a pre-trained CNN for CT scans is an example of transfer learning. However, the CNN 102 may be a pre-trained CNN that is additionally trained, for example using additional images that are not part of the ImageNet dataset. These additional images may be obtained from other datasets, either public or private. Of particular relevance to detecting HIBI are public databases that include CT brain scans, such as the DeepLesion dataset. However, the CNN 102 need not be pre-trained, i.e., the CNN 102 may be trained by the same party that uses the CNN 102 to implement the method 100.

FIG. 2 illustrates a method 200 for identifying progression of hypoxic-ischemic brain injury (HIBI). The method 200 processes a sequence of $n_s$ slices 104(1), 104(2), . . . , 104($n_s$). that is also referred to herein as a scan 204. The method 200 includes a block 206 that processes each slice 104($i$) to generate one corresponding slice-level feature vector 110($i$). The method 100 of FIG. 1 is one example of the block 206. The block 206 repeats $n_s$ times to generate $n_s$ slice-level feature vectors 110 in one-to-one correspondence with the $n_s$ slices 104 of the scan 204. The slice-level feature vectors 110 collectively form a sequence 210.

The method 200 includes a block 220 in which the sequence 210 is axially pooled to create a scan-level feature vector 222. Here, "axially" pooled means that each element of the scan-level feature vector 222 is pooled from the similarly-indexed elements of the slice-level feature vectors 110. This pooling may be average pooling, max pooling, or min pooling.

The method 200 also includes a block 224 in which the scan-level feature vector 222 is transformed into a reduced-dimensionality scan-level feature vector 226. The scan-level feature vector 222 has the same number of elements as each of the slice-level feature vectors 110 (e.g., 16,709 for the example of VGG19). To reduce dimensionality, a non-square projection matrix (e.g., see the projection matrix 350 in FIG. 3) may be multiplied by the scan-level feature vector 222 to produce the reduced-dimensionality scan-level feature vector 226. The projection matrix may have been previously constructed using principal component analysis (PCA), autoencoding, discriminant analysis, or another type of dimensionality-reduction technique.

In some embodiments, the projection matrix is generated as part of the method 200. For example, several training scans 204 may be used to create several scan-level feature vectors 222. PCA may then be performed on these scan-level feature vectors 222 to identify the largest principal components (i.e., the eigenvectors of the covariance matrix having the largest eigenvalues). Remaining components may be discarded and the projection matrix can then be constructed from the retained principal components.

The method 200 also includes a block 228 in which the reduced-dimensionality scan-level feature vector 226 is inputted to a trained classifier (e.g., see classifier 346 in FIG. 3) to obtain a score 230 indicating HMI progression. The trained classifier may be a support vector machine (SVM), a neural network, or another type of statistical or machine-learning classification model that is trained to output the score 230. The classifier may have been trained by a third party. In some embodiments, the classifier is trained as part of the method 200. For example, the classifier may be trained using reduced-dimensionality scan-level feature vectors 226 obtained from corresponding training scans 204.

Reducing the dimensionality of the scan-level feature vector 222 can improve the performance of the classifier by avoiding the curse of dimensionality and reducing the computational resources necessary for execution. However, dimensionality reduction is not necessary if the scan-level feature vector 222 is sufficiently low-dimensional. Accordingly, in some embodiments, the method 200 excludes the block 224, in which case the block 228 receives the scan-level feature vector 222 as its input.

In some embodiments, the method 200 includes the block 232 in which an endotype 234 is identified based on the score 230. The endotype 234 may be a first endotype indicating an absence of HIBI, or a second endotype indicating the presence of HIBI. The endotype 234 may be determined, for example, by comparing the score 230 to a threshold. The endotype 234 may form part of a diagnosis used to determine a therapy for the patient.

Figure 3:
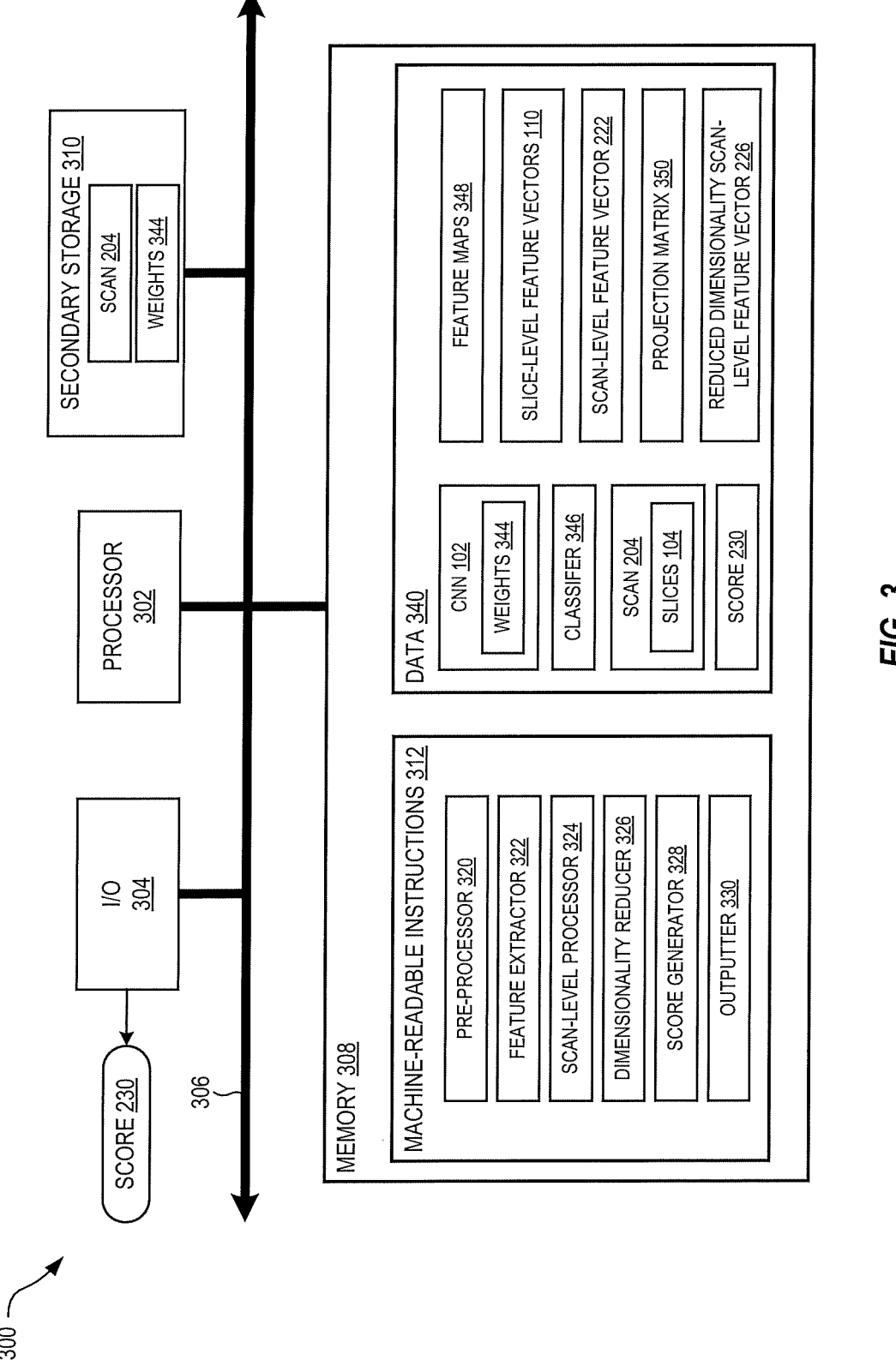
FIG. 3 is a diagram of an HIBI-prediction system that implements the present method embodiments.

FIG. 3 is a diagram of an HIBI-prediction system 300 that implements the present method embodiments. The HIBI-prediction system 300 is a computing device having a processor 302, a memory 308, and a secondary storage device 310 that communicate with each other over a system bus 306. For example, the memory 308 may be volatile RAM located proximate to the processor 302, while the secondary storage device 310 may be a hard disk drive, a solid-state drive, an optical storage device, or another type of persistent data storage. The secondary storage device 310 may alternatively be accessed via an external network instead of the system bus 306. Additional and/or other types of the memory 308 and the secondary storage device 310 may be used without departing from the scope hereof.

The HIBI-prediction system 300 may include at least one I/O block 304 that outputs the score 230 to a peripheral device (not shown). The I/O block 304 is connected to the system bus 306 and therefore can communicate with the processor 302 and the memory 308. In some embodiments, the peripheral device is a monitor or screen that displays the score 230 in a human-readable format (e.g., as a number). Alternatively, the I/O block 304 may implement a wired network interface (e.g., Ethernet, Infiniband, Fibre Channel, etc.), wireless network interface (e.g., WiFi, Bluetooth, BLE, etc.), cellular network interface (e.g., 4G, 5G, LTE), optical network interface (e.g., SONET, SDH, IrDA, etc.), multi-media card interface (e.g., SD card, Compact Flash, etc.), or another type of communication port through which the HIBI-prediction system 300 can communicate with another device.

The processor 302 may be any type of circuit or integrated circuit capable of performing logic, control, and input/output operations. For example, the processor 302 may include one or more of a microprocessor with one or more central processing unit (CPU) cores, graphics processing unit (GPU), digital signal processor (DSP), field-programmable gate array (FPGA), system-on-chip (SoC), microcontroller unit (MCU), and application-specific integrated circuit (ASIC). The processor 302 may also include a memory controller, bus controller, and other components that manage data flow between the processor 302, the memory 308, and other devices communicable coupled to the bus 306. Although not shown in FIG. 3, the HIBI-prediction system 300 may include a co-processor (e.g., a GPU, FPGA, or machine-learning accelerator) that is communicably coupled with the processor 302 over the bus 306. The co-processor may assist with execution of one or both of the CNN 102 and the classifier.

The memory 308 stores machine-readable instructions 312 that, when executed by the processor 302 (and co-processor, when present), control the HIB-prediction system 300 to implement the functionality and methods described herein. The memory 308 also stores data 340 used by the processor 302 (and co-processor, when present) when executing the machine-readable instructions 312. In the example of FIG. 3, the data 340 includes the CNN 102 (including weights 344), a classifier 346, the slices 104 of the scan 204, the score 230, feature maps 348 (e.g., the feature maps 112, 114, 116, 118, and 120), the slice-level feature vectors 110, the scan-level feature vector 222, a projection matrix 350, and the reduced-dimensionality scan-level feature vector 226. The memory 308 may store additional data 340 than shown. In addition, some or all of the data 340 may be stored in the secondary storage device 310 and fetched from the secondary storage device 310 when needed. In the example of FIG. 3, the secondary storage device 310 stores the scan 204 and the CNN weights 344.

In the example of FIG. 3, the machine-readable instructions 312 include a preprocessor 320, a feature extractor 322, a scan-level processor 324, a dimensionality reducer 326, a score generator 328, and an outputter 330. The preprocessor 320 processes each slice 104 prior to generating the slice-level feature vectors 110 (i.e., execution of the feature extractor 322). The preprocessor 320 may perform cropping, scaling, filtering, windowing (e.g., between 0 and 80 HU), segmenting, or a combination thereof. The feature extractor 322 then implements the method 100 by processing each slice 104 to extract feature maps from the CNN 102, pool and flatten the feature maps, and concatenate the resulting one-dimensional arrays to generate one of the slice-level feature vectors 110. The scan-level processor 324 implements the method 200 by pooling the slice-level feature vectors 110 to obtain the scan-level feature vector 222. The dimensionality reducer 326 transforms the scan-level feature vector 222 into the reduced-dimensionality scan-level feature vector 226 (e.g., my multiplying the scan-level feature vector 222 with the projection matrix 350). The score generator 328 inputs the reduced-dimensionality scan-level feature vector to a trained classifier to obtain the score 230. The outputter 330 then outputs the score 230 (e.g., to another computing system via the I/O block 304). Alternatively, or additionally, the outputter 330 may output one or more of the feature maps 348, slice-level feature vectors 110, scan-level feature vector 222, reduced-dimensionality scan-level feature vector 226, and other data 340. The memory 308 may store additional machine-readable instructions 312 than shown in FIG. 3 without departing from the scope hereof.

In some embodiments, the HIBI-prediction system 300 is incorporated into a CT scanner. In these embodiments, the HIBI-prediction system 300 may cooperate with the CT scanner to receive the scan 204 and output the score 230. In other embodiments, the HIBI-prediction system 300 is separate from the CT scanner. In these embodiments, the HIBI-prediction system 300 may communicate with the CT scanner (e.g., via an Ethernet connection) to receive the scan 204. In other embodiments, the HIBI-prediction system 300 operates independently of any CT scanner. For example, the HIBI-prediction system 300 may download the scan 204 from a server, memory stick, or flash drive on which the scan 204 is stored.

While the present embodiments have been described as operating with a CT scan, the present embodiments may also be used with another type of topographic medical imaging technique, such as magnetic resonance imaging (MRI), positron emission tomography (PET), ultrasonography, optical coherent tomography, photoacoustic tomography, and single-photon emission computed tomography (SPECT). Furthermore, while the above embodiments have been described as processing two-dimensional slices of a three-dimensional medical image, the voxels of the three-dimensional medical image may be partitioned in any other way without departing from the scope hereof.

Demonstration

Study COHORT

This is a case0-control analysis of patients who suffered cardiac arrest, be it in the hospital or outside the hospital, in the time period between October 2017 and March 2020. The Institutional Review Board of the University of Chicago approved the protocol (IRB 200,107). For this type of study, formal consent was not required. Inclusion criteria for the study were as follows: (1) presenting diagnosis of cardiac arrest, (2) age greater than or equal to 18 years, (3) unresponsive (comatose status) after ROSC, (4) noncontrast HCT imaging performed within 24 hours of admission and deemed normal with no stigmata of HIBI by a board-certified neuroradiologist (in particular, no evidence of sulcal effacement, loss of gray-white matter differentiation, or compromise of cisternal spaces), and (5) available repeat HCT imaging within 2 to 10 days from the initial HCT scan. The following were the exclusion criteria: (1) dead on arrival, (2) failure to achieve return of spontaneous circulation (ROSC), and (3) absence of HCT imaging within 24 hours from arrest or absence of follow-up HCT imaging within 10 days from that time. Although all patients had an initial HCT scan that was interpreted as lacking any signs of HIBI by a board-certified neuroradiologist, cases were defined as patients who suffered development of HIBI on repeat imaging and controls were patients who did not develop HIBI and continued to be interpreted as having no signs of HIBI. HIBI was defined on imaging as any evidence of sulcal effacement, loss of gray-white matter differentiation, or compromise of cisternal spaces.

Data Collection

For each patient, data regarding demographics, clinical presentation, Glasgow Coma Scale (GCS) scores, HCT scans on admission and follow-up, time intervals from presentation to initial imaging, time interval between HCT scans, laboratory studies, hospital length of stay, and discharge disposition were reviewed.

HCT images were reviewed by a board-certified neuroradiologist. Patients were categorized into two groups according to radiological reports of their follow-up HCT imaging. The first group included patients whose presenting HCT imaging results were evaluated and deemed lacking any signs of HIBI and whose follow-up imaging maintained that status (no CT progression, or "NCTProg"). The second group included patients whose presenting HCT imaging results were also deemed lacking any signs of HIBI; however, the follow-up imaging results were deemed as showing signs of HIBI (CT progression, or "CTProg"). This was a retrospective evaluation of reports by neuroradiologists. No specific instructions regarding imaging review windows were dictated. Furthermore, reports commenting on chronic findings, such as stigmata of small vessel disease, chronic subdural collections, atrophy, or prior surgical interventions, were not factored as abnormalities. The purpose of the aforementioned was to best depict real-life practice and to not bias readers by the purpose of the current study.

Deep Transfer Learning

CT scans were windowed with a standard brain window with center 40 HU and width 40 HU, and CT slices presenting no brain anatomy were excluded from analysis. The transfer learning approach used in this study was based on methods described by Antropova et al. (Antropova N, Huynh B Q, Giger M L. A deep feature fusion methodology for breast cancer diagnosis demonstrated on three imaging modality datasets. Med Phys. 2017; 44(10):5162-71), which were expanded to account for the three-dimensional information available in CT scans. Briefly, a VGG19 network architecture pretrained on the ImageNet database (a collection of millions of natural non-medical images) was used to extract quantitative features from only the initial HCT scan (no follow-up information included) (see FIG. 4). The mean value of each feature map produced by the maximum pooling layers was used to form a normalized representative feature vector for each individual CT slice. These vectors were maximum pooled in the axial dimension for all slices within a scan to obtain a scan-level representation.

Figure 4:
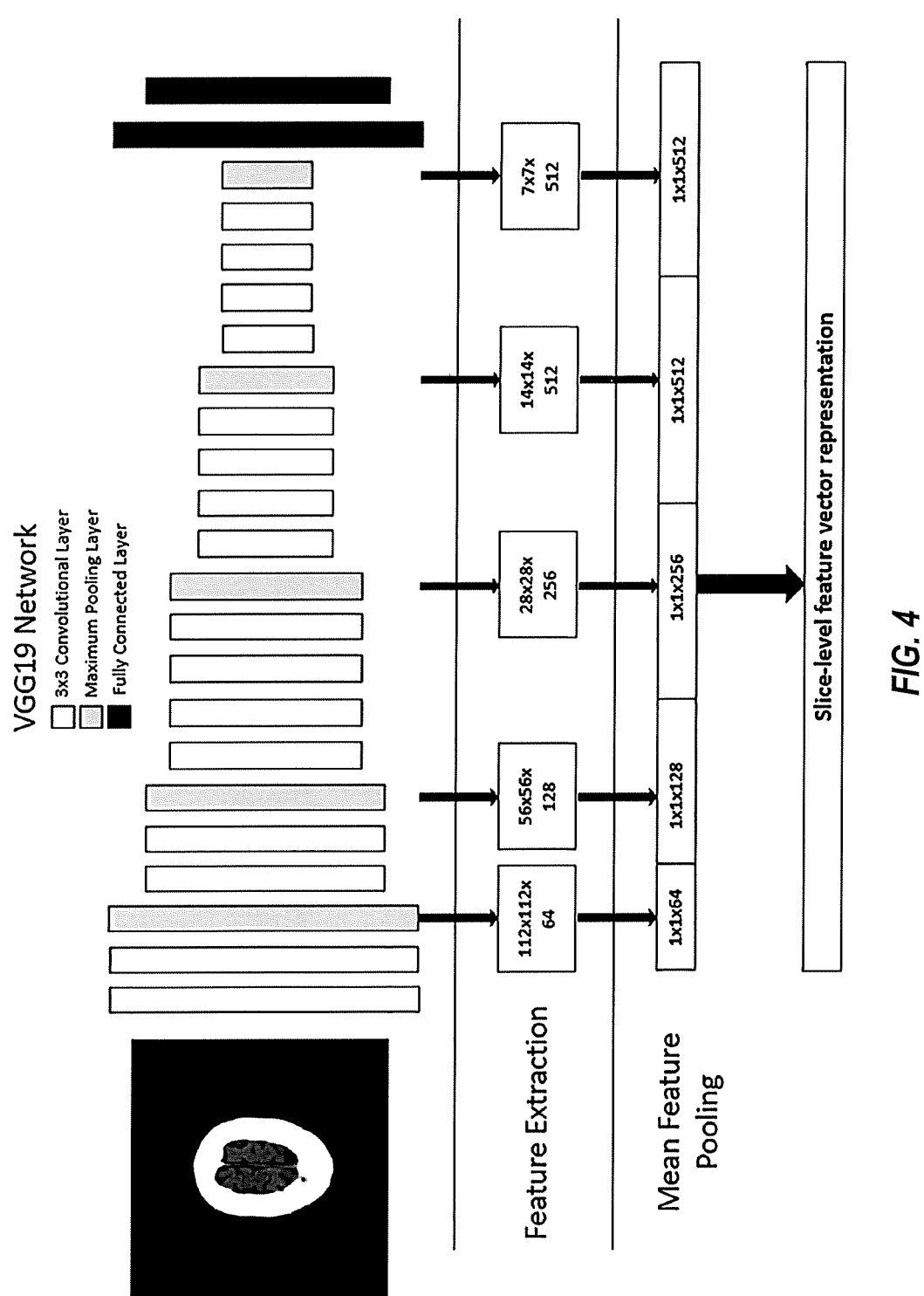
FIG. 4 is a diagram of a deep transfer learning technique used to examine individual head computed tomography slices, in an embodiment.
Figure 5:
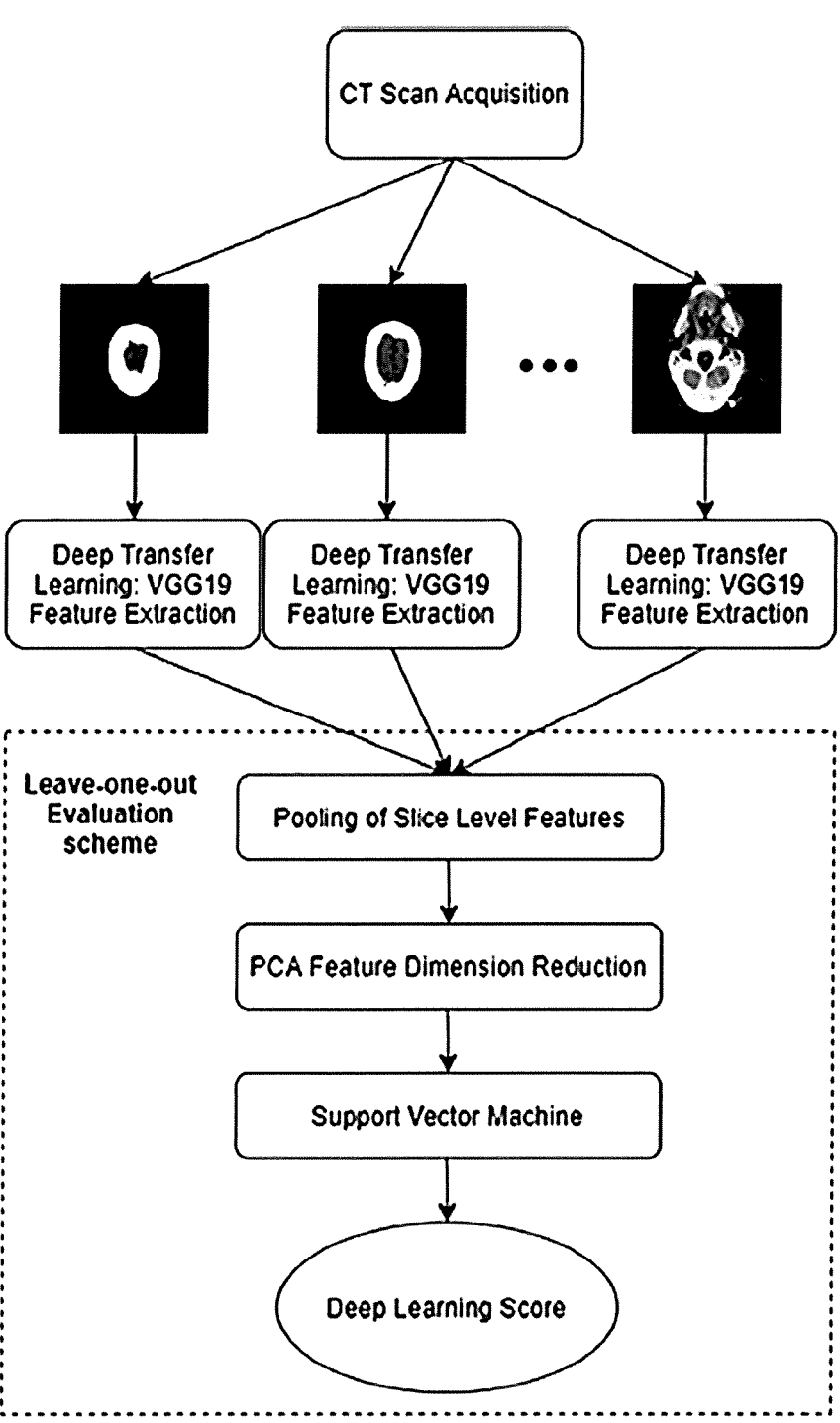
FIG. 5 is a block diagram of a deep transfer learning pipeline that includes VGG19-based feature extraction, feature dimension reduction through principal component analysis (PCA), and evaluation through a support vector machine.

Because of the limited data in this study, leave-one-out-by-patient cross-validation was used. Principal component analysis was performed on 53 of the 54 available scans for dimensionality reduction in an attempt to alleviate the risk of model overfitting. Then a support vector machine (SVM) was trained by using the principal components for the task of classifying a scan as progressive (exhibited or would exhibit signs of HIBI on follow-up HCT scan) or nonprogressive (no signs of HIBI on follow-up HCT scan). The single scan that was not included in the training set was then evaluated by using the SVM. This process of principal component analysis, SVM training, and single-scan testing was repeated so that each of the 54 scans served as the test scan exactly one time, and a prevalence scaling factor was applied to correct for class imbalance in the data set. This full workflow is depicted in FIGS. 4 and 5, with the predicted SVM output probability serving as a scan-level deep learning score (DLS) as the pipeline output.

To validate the performance of the deep transfer learning technique, an additional independent test set composed of four CTProg and twelve NCTProg scans was evaluated by using the SVM trained with all 54 scans.

Statistical Analysis

Descriptive statistics were presented as means with standard deviations or medians with interquartile ranges (IQRs) (as appropriate) for continuous variables and as percentages for categorical variables. In univariate analyses, categorical variables were compared by using Fisher's exact test. A significance level was set at p<0.05. All analyses were performed with the use of Python programming language and R version 3.6.1.

SVM classification performance between patients with CTProg and NCTProg was evaluated with receiver operating characteristic (ROC) curve analysis, with the area under the ROC curve (AUC) as the figure of merit. AUC confidence intervals (CIs) were determined through 1,000 bootstrapping resampling iterations. Note that because of the relatively small amount of data, some bootstrap iterations of the validation set only contained NCTProg and were thus ignored.

Results

FIG. 7 is a table summarizing results of the study. The following abbreviations are used in FIG. 7:

CT: computed tomography
CTProg: CT progression
DLS: deep learning score
GCS Glasgow Coma Scale
GCS-M: Glasgow Coma Scale-Motor
IQR: interquartile range
NCTProg: no CT progression
ROSC: return of spontaneous circulation
TTM: targeted temperature management
VOR: vestibulo-ocular reflex:
WLST: withdrawal of life-sustaining therapy The asterisks in FIG. 7 indicate p-values below 0.05.

Basic Characteristics of the Population: FIG. 7 shows the basic characteristics of the population. Overall, 54 patients were included in the analysis. The median age (IQR) of the cohort was 61 (16) years, and 25 patients (46%) were female. The predominant race was Black, with 44 patients (81%). The median time to achieving ROSC was 22 (23) minutes.

Clinical Features on Initial Neurological Assessment: Among the 54 patients, the median GCS score (IQR) was 3 (3). At least one reactive pupil was appreciated in 43 patients (80%). At least one corneal reflex was appreciated in 29 patients (56%). A cough or gag reflex was pre-sent in 34 patients (64%), and an oculocephalic reflex was appreciated in 26 patients (52%). Thirty-seven patients (68%) were breathing over the ventilator. The median motor component of the GCS score was 1 (no motor response). Finally, 30 patients (56%) suffered from myo-clonus (see FIG. 7). The median time from arrest to initial HCT scan in the entire cohort was 3 (2-17) hours. The median time between the first and follow-up HCT scan was 2 (2-7) days.

Comparing CTProg and NCTProg Cohorts: Twenty-nine of the 54 patients had a follow-up HCT scan that demonstrated progression (CTProg), compared with 25 patients who did not (NCTProg) (see FIG. 7). The median time from cardiac arrest to initial HCT scan and the time between first and follow-up HCT scans was not different across the two groups (Mann-Whitney U-test, p=0.408 and p=0.398, respectively). The CTProg group had a median GCS score of 3 (2), compared with 6 (4) in the NCTProg group (p=0.011). Targeted temperature management was done in 27 (93%)

patients with CTProg, compared with 17 (68%) patients with NCTProg (p=0.018) (see FIG. 7).

Mortality and Mechanism of Death: Of the 54 patients, 34 (63%) died in-house. Those included 12 (48%) patients whose CT imaging results did not progress and 22 (76%) whose CT imaging results progressed serially (p=0.035). The mechanism of death was withdrawal of life-sustaining therapies in 18 (82%) patients with CTProg, compared with 12 (100%) patients with NCTProg (p=0.107). Cardiac death occurred in 2 (9%) patients with CTProg, compared with 0 (0%) patients with NCTProg (p=0.27). Two (9%) patients with CTProg were declared brain dead, compared with 0 (0%) patients with NCTProg (p=0.27) (see FIG. 7).

Figure 6:
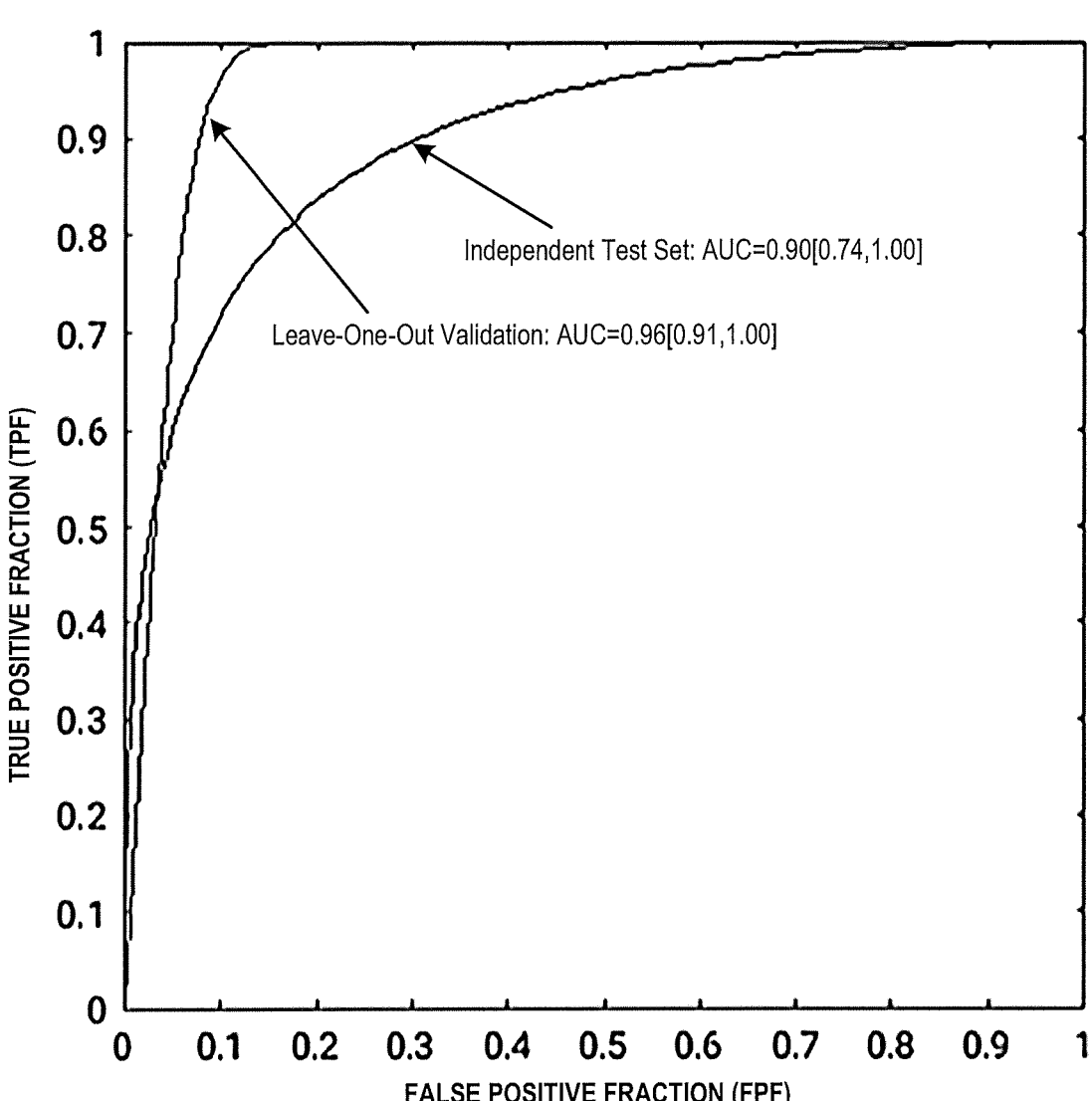
FIG. 6 is a plot showing receiver operating characteristic (ROC) curves for the leave-one-out cross-validation approach and the independent test set in the task of distinguishing between patients with CTProg and NCTProg obtained by using a proper binormal model, with confidence intervals calculated through bootstrapping.

Assessment of the Machine Learning Algorithm: In the task of distinguishing between patients with CTProg and NCTProg, the AUC was 0.96 (95% CI 0.91-1.0). The ROC curve is shown in FIG. 6. The prevalence-scaled optimal operating point of the ROC curve was found to be a DLS of 0.494. Operating at this threshold, performance included a sensitivity of 1.00, specificity of 0.88, accuracy of 0.94, and positive predictive value of 0.91. In evaluating the additional test set of 16 scans (4 CTProg and 12 NCTProg) and operating at the same DLS threshold of 0.494, the AUC was 0.90 (95% CI 0.74-1.00), with optimal operating performances (sensitivity=1.00, specificity=0.66, accuracy=0.75, and positive predictive value=0.5).

Comparing Clinical Variables with DLS in HIBI Prediction: FIG. 7 shows that the difference in DLS is more significant than that of other variables. In a multiple variable logistic regression assessing DLS, pupillary reactivity, corneal reaction, VOR, and GCS score, DLS is the only variable significantly associated with progression (coefficient 275.35 [95% CI 106.826-443.875], p<0.01).

Discussion

In this single-center study, we demonstrate that deep transfer learning can accurately identify a HCT signature of HIBI within the first three hours after ROSC in comatose survivors of a cardiac arrest. The determination and quantification of HIBI is a cornerstone of neuroprognostication in survivors of cardiac arrest. Similarly, it plays a determinant role in the shared decision-making process that often culminates in withdrawal of life-sustaining therapies in this patient population.

Our findings indicate that (1) a degree of identifiable injury to the brain may have already occurred in a number of patients who present normal-appearing findings on early HCT and (2) a significant number of patients presenting normal-appearing findings on HCT per-formed, on average, within the first three hours after ROSC demonstrate significant abnormalities when HCT scans are evaluated with deep transfer learning.

Consideration for Early Distinction of Specific Endotypes of Cardiac Arrest Survivors: Our findings indicate that when early (within three hours of RO SC) HCT scans with normal-appearing results are analyzed with deep transfer learning, two unique endotypes of cardiac arrest survivors can be identified: one type that bares no features of HIBI and one that does. Because many of the therapies applied following ROSC intend to improve neurological outcomes, we suggest that the early stratification of survivors of cardiac arrest into these two distinct endotypes could serve to optimize the selection process of patients for clinical trials in the future. This model could help select patients who do not exhibit early radiographic HIBI because this endotype is, arguably, more likely to benefit from early interventions aimed at preventing further hypoxic-ischemic brain damage.

In addition, if our findings are prospectively reproduced and, at the same time, HCT progression (or presence of radiographic HIBI) is proven to definitively correlate with poor neurological outcome, we could also suggest that discussions about neurological prognosis with patients' surrogate decision makers could begin earlier than currently recommended.

Significance of Early Identification of Radiographic Brain Injury: The ability of the model to identify patients who will progress to radiographically discernable HIBI from those who will not, suggests that early on, changes on HCT already exist, albeit too subtle to discern by the human eye. Because substantial interobserver variability when identifying HIBI on HCT soon after out-of-hospital cardiac arrest has been reported, we verified that the CTProg and NCTProg groups were not evaluated by any one specific radiologist. As a matter of fact, a total of ten different radiologists composed the pool that evaluated the first scans. All those scans were read as normal, and the CTProg versus NCTProg determination was not more likely with any one particular radiologist.

The success of the automatic method in distinguishing patients with CTProg from those with NCTProg, particularly in the independent test set, suggests the presence of unique features within the images of the two cohorts. Given the presumed hypoxic-ischemic mechanism of brain injury, this finding can be interpreted in two different ways. The first is that HIBI might have already occurred to its full extent at the time of the initial HCT scan. If true, this would suggest that neuro-protective interventions started at this time could be of questionable utility. The injury would be potentially unmodifiable and determined by the clinical and temporal features of the cardiac arrest as well as the individual patient's profile.

On the other hand, it is possible that some patients have suffered some degree but not the full extent of hypoxic-ischemic injury. The injury is, therefore, a step along a potentially modifiable pathway. In other words, although a degree of injury might have occurred, its progression and outcome could be potentially modified by neuroprotective therapeutic measures. The model could help detect the patient population that is along this path and for which medical optimization may be more critical.

Although it is also possible that the early identification of brain injury with machine learning allows for a discrimination between different degrees of brain injury in the first few hours after ROSC, we have not quantified the degree of radiographic brain injury in follow-up HCT scans and therefore cannot comment on the potential discriminative power of the applied machine learning strategy in these two clinical scenarios. Furthermore, clinical characteristics, such as physical examination findings (GCS score, pupillary reactivity, and corneal reflexes), have been shown to correlate with neurological outcome, and although those variables are indeed different in our cohort of patients, the purpose of this study is to emphasize the unique role of early HCT imaging in identifying HIBI progression and not to replace the aforementioned clinical variables. To further understand the contribution of the DLS to prediction of HIBI progression, we conducted a pilot study using our clinical variables; a classifier based purely on the clinical variables without the DLS had an AUC of approximately 0.76, compared with a classifier based on the DLS alone, which had an AUC of ~0.96. Adding the clinical variables to the DLS in a combined classifier does not improve the AUC. That being said, a model incorporating clinical as well as radiographic features is out of the scope of the cur-rent work but is indeed the subject of future prospective research.

Our model does not predict mortality or withdrawal of life-sustaining therapies. It evaluates HCT images that are assessed as lacking signs of HIBI by the human eye and defines the cohort that will progress to show stigmata of HIBI on repeat imaging. In other words, it deter-mines early on what HCT images bear features of HIBI that are not readily discernable by the human operator.

Limitations

This is a single-center study that will need prospective and multicenter validation. Also, the lack of a universally accepted radiographic definition of HIBI after cardiac arrest makes us rely on our neuroradiologists' assessments of HIBI on HCT in accordance with prior relevant literature.

Additionally, because of the limited size of both the training and independent test data sets, there is a possibility for model overfitting and bias. Despite the promising results in both the leave-one-out-by-patient cross-validation technique and independent test set evaluation, a large diverse independent testing set is needed to further validate these results. The dynamic range of the DLS is small. There are multiple factors that could contribute to this phenomenon. First, the task itself indicates that the HCT images are similar, with all scans read as normal by a board-certified radiologist; thus, we expect that the embedded representations in feature space are clustered closely together, both within and between the NCTProg and CTProg populations. A second potential cause is the limited amount of data causing overfitting in the model and thus introducing a biased evaluation. Although we have attempted to alleviate the concern of significant overfitting by demonstrating strong performance on the limited validation set and through CI estimation through bootstrapping, we acknowledge that there is still potential for a biased model. We are currently working to acquire a larger prospective data set for validation, but this lies outside the scope of this study. Given superior MRI sensitivity, it is indeed possible that some of the patients on presentation or follow-up HCT labeled as lacking radiographic signs of HIBI may have had HIBI on MRI. However, the particular focus of the study is to optimize CT interpretive potential and not claim any comparison or superiority to MRI.

CONCLUSIONS

Deep transfer learning reliably identifies HIBI in normal-appearing findings on HCT performed within three hours after ROSC in comatose survivors of a cardiac arrest. This may suggest the presence of two distinct and identifiable endotypes of brain injury in this population, opening the door for more individualized treatment algorithms as well as providing a potential for early determination of neurological outcome. In addition to prospective validation, next steps of this work will include prospective patient cohorts with MRI and HCT imaging obtained and analyzed in tandem as well as incorporation of clinical variables into a combined clinical-imaging model.

Combination of Features

Features described above as well as those claimed below may be combined in various ways without departing from the scope hereof. The following examples illustrate possible, non-limiting combinations of features and embodiments described above. It should be clear that other changes and modifications may be made to the present embodiments without departing from the spirit and scope of this invention:

(A1) A method for identifying the presence or progression of hypoxic ischemic brain injury (HIBI includes, for each subset of one or more subsets of a three-dimensional medical image of a head of a patient: (i) inputting said each subset into a machine-learning model, (ii) extracting one or more features or feature maps from the machine-learning model, and (iii) constructing, based on the one or more features or feature maps, one of a sequence of vectors. The method also includes pooling the sequence of vectors to obtain a scan-level vector and using the scan-level vector to obtain a score indicating HIBI presence or progression.

(A2) In the method denoted (A1), said using the scan-level vector includes transforming the scan-level vector into a reduced-dimensionality scan-level vector and inputting the reduced-dimensionality scan-level vector to a classifier to obtain the score indicating HIBI presence or progression.

(A3) In the method denoted (A2), the classifier includes a support-vector machine.

(A4) In the method denoted (A3), the method further includes training the support-vector machine using a plurality of training scan-level feature vectors obtained from a corresponding plurality of training medical images.

(A5) In any of the methods denoted (A2)-(A4), said transforming includes multiplying the scan-level vector by a projection matrix to obtain the reduced-dimensionality scan-level vector.

(A6) In the method denoted (A5), the method further includes generating the projection matrix by applying principal component analysis to a plurality of training scan-level feature vectors obtained from a plurality of training medical images.

(A7) In any of the methods denoted (A1)-(A6), said constructing comprises, for each of the one or more feature maps: determining a mean value of said each of the one or more feature maps and appending the mean value to said one of the sequence of vectors.

(A8) In any of the methods denoted (A1)-(A7), the method further includes normalizing said one of the sequence of vectors.

(A9) In any of the methods denoted (A1)-(A8), said pooling includes max-pooling.

(A10) In any of the methods denoted (A1)-(A9), the machine-learning model includes a neural network.

(A11) In the method denoted (A10), the neural network is a VGG neural network.

(A12) In the method denoted (A11), the VGG neural network is a VGG19 neural network.

(A13) In any of the methods denoted (A10)-(A12), said extracting includes extracting the one or more features or feature maps from one or more max-pooling layers of the neural network.

(A14) In any of the methods denoted (A1)-(A13), the machine-learning model has been trained on the ImageNet database.

(A15) In any of the methods denoted (A1)-(A14), the machine-learning model has been trained using medical images from each training patient of a plurality of training patients. One or more of the medical images of said each training patient are obtained no less than three hours after said each training patient's return of spontaneous circulation following cardiac arrest.

(A16) In the method denoted (A15), one or more of the medical images of said each patient are obtained no less than twenty-four hours after said each patient's return of spontaneous circulation following cardiac arrest.

(A17) In any of the methods denoted (A1)-(A16), the method further includes identifying, based on the score, one of a first endotype indicating absence of HIBI and a second endotype indicating presence of HIBI.

(A18) In the method denoted (A17), the method further includes treating the patient based on the first endotype or the second endotype.

(A19) In any of the methods denoted (A1)-(A18), the method further includes capturing the three-dimensional medical image of the head of the patient.

(A20) In the method denoted (A19), said capturing occurs within three hours of return of spontaneous circulation following cardiac arrest.

(B1) A system for identifying progression of hypoxic-ischemic brain injury (HIBI) includes a processor, a memory communicably coupled with the processor, and a machine-language model implemented as machine-readable instructions stored in the memory. The system also includes an HIBI predictor implemented as machine-readable instructions that are stored in the memory and, when executed by the processor, control the system to, for each subset of one or more subsets of a three-dimensional medical image of a head of a patient: (i) input said each subset into a machine-learning model, (ii) extract one or more features or feature maps from the machine-learning model, and (iii) construct, based on the one or more features or feature maps, one of a sequence of vectors. The machine-readable instructions also control the system to pool the sequence of vectors to obtain a scan-level vector and use the scan-level vector to obtain a score indicating HIBI presence or progression.

(B2) In the system denoted (B1), the machine-readable instructions that, when executed by the processor, control the system to use the scan-level vector include machine-readable instructions that, when executed by the processor, control the system to transform the scan-level vector into a reduced-dimensionality scan-level vector and feed the reduced-dimensionality scan-level vector to a classifier to obtain the score indicating HIBI presence or progression.

(B3) In the system denoted (B2), the classifier includes a support-vector machine.

(B4) In any of the systems denoted (B1)-(B3), the machine-learning model is a neural network.

(B5) In the system denoted (B4), the neural network is a VGG neural network.

(B6) In either of the systems denoted (B4) and (B5), the machine-readable instructions that, when executed by the processor, control the system to extract the scan-level vector include machine-readable instructions that, when executed by the processor, control the system to extract the one or more features or feature maps from one or more max-pooling layers of the neural network.

(B7) In any of the systems denoted (B1)-(B6), the machine-learning model has been trained on the ImageNet database.

(B8) In any of the systems denoted (B1)-(B7), the machine-learning model has been trained using medical images from each training patient of a plurality of training patients, wherein one or more of the medical images of said each training patient are obtained no less than three hours after said each training patient's return of spontaneous circulation following cardiac arrest.

(B9) In the system denoted (B8), one or more of the medical images of said each training patient are obtained no less than twenty-four hours after said each training patient's return of spontaneous circulation following cardiac arrest.

(B10) In any of the systems denoted (B1)-(B9), the HIBI predictor stores additional machine-readable instructions that, when executed by the processor, control the system to identify, based on the score, one of a first endotype indicating absence of HIBI and a second endotype indicating presence of HIBI.

(C1) A method for identifying progression of hypoxic-ischemic brain injury (HIBI) includes, for each slice of a sequence of slices forming a computed tomography (CT) scan of a head of a patient: (i) inputting said each slice into a trained convolutional neural network, (ii) extracting one or more feature maps from the trained convolutional neural network, and (iii) constructing, based on the one or more feature maps, one of a sequence of slice-level feature vectors. The method also includes pooling the sequence of slice-level feature vectors to obtain a scan-level feature vector and feeding the scan-level feature vector to a trained classifier to obtain a score indicating HIBI progression.

(C2) In the method denoted (C1), the method further includes transforming the scan-level feature vector into a reduced-dimensionality scan-level feature vector. Said feeding includes feeding the reduced-dimensionality scan-level feature vector to the trained classifier.

(C3) In the method denoted (C2), said transforming includes multiplying the scan-level feature vector by a projection matrix.

(C4) In the method denoted (C3), the method further includes generating the projection matrix by applying principal component analysis to a plurality of training scan-level feature vectors obtained from a corresponding plurality of training CT scans.

(C5) In any of the methods denoted (C1)-(C4), said constructing includes, for each of the one or more feature maps: (i) determining a mean value of said each of the one or more feature maps and (ii) appending the mean value to said one of the sequence of slice-level feature vectors.

(C6) In the method denoted (C5), the method further includes normalizing said one of the sequence of slice-level feature vectors.

(C7) In any of the methods denoted (C1)-(C6), said pooling includes max-pooling.

(C8) In any of the methods denoted (C1)-(C7), the trained convolutional neural network is a VGG neural network.

(C9) In the method denoted (C9), the trained convolutional neural network is a VGG19 neural network.

(C10) In any of the methods denoted (C1)-(C9), said extracting includes extracting the one or more feature maps from one or more max-pooling layers of the trained convolutional neural network.

(C11) In any of the methods denoted (C1)-(C10), the convolutional neural network has been trained on the ImageNet database.

(C12) In any of the methods denoted (C1)-(C10), the trained classifier is a support-vector machine.

(C13) In the method denoted (C12), the method further includes training the support-vector machine using a plurality of a plurality of training scan-level feature vectors obtained from a corresponding plurality of training CT scans.

(C14) In any of the methods denoted (C1)-(C13), the method further includes identifying, based on the score, one of a first endotype indicating absence of HIBI and a second endotype indicating presence of HIBI.

(C15) In the method denoted (C14), the method further includes treating the patient based on the first endotype or the second endotype.

(C16) In any of the methods denoted (C1)-(C15), the method further includes capturing the CT scan.

(C17) In the method denoted (C16), said capturing occurs within three hours of return of spontaneous circulation after cardiac arrest.

(D1) A system for identifying progression of hypoxic-ischemic brain injury (HIBI) includes a processor, a memory communicably coupled with the processor, a trained convolutional neural network implemented as machine-readable instructions stored in the memory, and a trained classifier implemented as machine-readable instructions stored in the memory. The system also includes an HIBI predictor implemented as machine-readable instructions that are stored in the memory and, when executed by the processor, control the system to, for each slice of a sequence of slices forming a computed tomography (CT) scan of a head of a patient: (i) input said each slice into the trained convolutional neural network, (ii) extract one or more feature maps from the trained convolutional neural network, and (iii) construct, based on the one or more feature maps, one of a sequence of slice-level feature vectors. The machine-readable instructions also control the system to pool the sequence of slice-level feature vectors to obtain a scan-level feature vector and feed the scan-level feature vector to the trained classifier to obtain a score indicating HIBI progression.

(D2) In the system denoted (D1), the HIBI predictor stores additional machine-readable instructions that, when executed by the processor, control the system to transform the scan-level feature vector into a reduced-dimensionality scan-level feature vector. The machine-readable instructions that, when executed by the processor, control the system to feed include machine-readable instructions that, when executed by the processor, control the system to feed the reduced-dimensionality scan-level feature vector to the trained classifier.

(D3) In either of the systems denoted (D1) and (D2), the memory stores additional machine-readable instructions that, when executed by the processor, control the system to output the score.

(D4) In any of the systems denoted (D1)-(D3), the memory stores additional machine-readable instructions that, when executed by the processor, control the system to communicate with a CT scanner to receive the CT scan.

(D5) In any of the systems denoted (D1)-(D4), the machine-readable instructions that, when executed by the processor, control the system to construct include machine-readable instructions that, when executed by the processor, control the system to, for each of the one or more feature maps: (i) determine a mean value of said each of the one or more feature maps and (ii) append the mean value to said one of the sequence of slice-level feature vectors.

(D6) In any of the systems denoted (D1)-(D5), the trained convolutional neural network is a VGG neural network.

(D7) In the system denoted (D6), the trained convolutional neural network is a VGG19 neural network.

(D8) In any of the systems denoted (D1)-(D7), the machine-readable instructions that, when executed by the processor, control the system to extract include machine-readable instructions that, when executed by the processor, control the system to extract the one or more feature maps from one or more max-pooling layers of the trained convolutional neural network.

(D9) In any of the systems denoted (D1)-(D8), the trained classifier is a support-vector machine.

(D10) In any of the systems denoted (D1)-(D9), the HIBI predictor includes additional machine-readable instructions that, when executed by the processor, control the system to identify, based on the score, one of a first endotype indicating absence of HIBI and a second endotype indicating presence of HIBI.

(D11) In the system denoted (D10), the memory storing additional machine-readable instructions that, when executed by the processor, control the system to output one of the first endotype and the second endotype.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method for identifying the presence or progression of hypoxic ischemic brain injury (HIBI), comprising:

for each subset of one or more subsets of a three-dimensional medical image of a head of a patient:

inputting said each subset into a machine-learning model;

extracting one or more feature maps from the machine-learning model; and constructing, based on the one or more feature maps, a respective one of a sequence of subset-level feature vectors;

pooling the sequence of subset-level feature vectors to obtain a scan-level feature vector; and using the scan-level feature vector to obtain a score indicating HIBI presence or progression.

2. The method of claim 1, wherein said using the scan-level feature vector includes:

transforming the scan-level feature vector into a reduced-dimensionality scan-level feature vector; and feeding the reduced-dimensionality scan-level feature vector into a classifier to obtain the score indicating HIBI presence or progression.

3. The method of claim 2, wherein the classifier includes a support-vector machine.

4. The method of claim 2, wherein said transforming includes multiplying the scan-level feature vector by a projection matrix to obtain the reduced-dimensionality scan-level feature vector.

5. The method of claim 1, wherein said constructing comprises:

for each of the one or more feature maps:

determining a mean value of said each of the one or more feature maps; and appending the mean value to the respective one of the sequence of subset-level feature vectors.

6. The method of claim 1, further comprising normalizing the respective one of the sequence of subset-level feature vectors.

7. The method of claim 1, wherein said pooling includes max-pooling.

8. The method of claim 1, the machine-learning model including a neural network.

9. The method of claim 8, wherein said extracting includes extracting the one or more feature maps from one or more max-pooling layers of the neural network.

10. The method of claim 1, further comprising identifying, based on the score, one of:

a first endotype indicating absence of HIBI; and a second endotype indicating presence of HIBI.

11. The method of claim 10, further comprising treating the patient based on the first endotype or the second endotype.

12. The method of claim 1, further comprising capturing the three-dimensional medical image of the head of the patient.

13. The method of claim 12, wherein said capturing occurs within three hours of return of spontaneous circulation following cardiac arrest.

14. A system for identifying progression of hypoxic-ischemic brain injury (HIBI), comprising:

a processor;

a memory communicably coupled with the processor;

a machine-language model implemented as machine-readable instructions stored in the memory; and an HIBI predictor implemented as machine-readable instructions that are stored in the memory and, when executed by the processor, control the system to:

for each subset of one or more subsets of a three-dimensional medical image of a head of a patient:

(i) input said each subset into a machine-learning model, (ii) extract one or more feature maps from the machine-learning model, and (iii) construct, based on the one or more feature maps, a respective one of a sequence of subset-level feature vectors, pool the sequence of subset-level feature vectors to obtain a scan-level feature vector, and use the scan-level feature vector to obtain a score indicating HIBI presence or progression.

15. The system of claim 14, wherein the machine-readable instructions that, when executed by the processor, control the system to use the scan-level feature vector include machine-readable instructions that, when executed by the processor, control the system to:

transform the scan-level feature vector into a reduced-dimensionality scan-level feature vector; and feed the reduced-dimensionality scan-level feature vector into a classifier to obtain the score indicating HIBI presence or progression.

16. The system of claim 15, wherein the classifier includes a support-vector machine.

17. The system of claim 14, the machine-learning model being a neural network.

18. The system of claim 17, the neural network being a VGG neural network.

19. The system of claim 17, wherein the machine-readable instructions that, when executed by the processor, control the system to extract include machine-readable instructions that, when executed by the processor, control the system to extract the one or more feature maps from one or more max-pooling layers of the neural network.

20. The system of claim 14, the HIBI predictor storing additional machine-readable instructions that, when executed by the processor, control the system to identify, based on the score, one of:

a first endotype indicating absence of HIBI; and a second endotype indicating presence of HIBI.

\* \* \* \* \*